US 6,592,373 B2

United States Patent
Zilberman

(10) Patent No.: US 6,592,373 B2
(45) Date of Patent: Jul. 15, 2003

(54) ACETAL RESIN CROWNS FOR CHILDREN

(76) Inventor: Uri L. Zilberman, 4 Eliyahu Meron Street, Nes Ziona (IL)

(*) Notice: Subject to any disclaimer, the term of this patent is extended or adjusted under 35 U.S.C. 154(b) by 0 days.

(21) Appl. No.: 09/903,096

(22) Filed: Jul. 11, 2001

(65) Prior Publication Data

US 2002/0150864 A1 Oct. 17, 2002

(30) Foreign Application Priority Data

Apr. 17, 2001 (IL) ................................................ 142657

(51) Int. Cl.$^7$ ................................................ A61C 5/08
(52) U.S. Cl. ................................................ 433/218
(58) Field of Search ................................ 433/218, 219, 433/222.1, 223, 202.1, 212.1

(56) References Cited

U.S. PATENT DOCUMENTS

| | | | | |
|---|---|---|---|---|
| 4,015,332 A | * | 4/1977 | Manne | 433/219 |
| 4,129,946 A | | 12/1978 | Kennedy | 32/63 |
| 4,215,033 A | | 7/1980 | Bowen | 260/42.15 |
| 4,381,918 A | | 5/1983 | Ehrnford | 433/199 |
| 4,433,959 A | | 2/1984 | Faunce | 433/201 |
| 4,678,435 A | * | 7/1987 | Long | 433/218 |
| 5,332,390 A | | 7/1994 | Rosellini | 433/34 |
| 5,346,397 A | * | 9/1994 | Braiman | 264/19 |
| 5,487,663 A | | 1/1996 | Wilson | 433/218 |
| 5,552,390 A | | 9/1996 | Scholar et al. | 514/44 |
| 5,624,261 A | | 4/1997 | Wiedenfeld | 433/222.1 |
| 5,709,548 A | | 1/1998 | Oxman et al. | 433/218 |
| 6,106,295 A | | 8/2000 | Wilson | 433/222.1 |
| 6,186,790 B1 | * | 2/2001 | Karmaker et al. | 433/180 |

FOREIGN PATENT DOCUMENTS

JP 11-262947 9/1999

OTHER PUBLICATIONS

*Dental D Acetal Resin*, 9/98 product brochure, Quattro Ti S.r.l., Tecnopolimeri Biomediali.

* cited by examiner

Primary Examiner—Kevin Shaver
Assistant Examiner—Melba Bumgarner
(74) Attorney, Agent, or Firm—Weingarten, Shurgin, Gagnebin & Lebovici LLP

(57) ABSTRACT

An injection molded dental crown formed of an acetal homopolymer resin.

A method for mass producing dental crowns is also disclosed.

3 Claims, 4 Drawing Sheets

FROM SOURCE OF ACETAL HOMOPOLYMER RESIN

ACETAL RESIN CROWNS FOR CHILDREN

FIELD OF THE INVENTION

The present invention relates to tooth prostheses generally and more particularly to crowns.

BACKGROUND OF THE INVENTION

The following U.S. Patents and publications are believed to represent the current state of the art: U.S. Pat. Nos. 4,129,946; 5,552,390; 5,487,663; 5,624,261; 5,709,548 and 6,106,295.

SUMMARY OF THE INVENTION

The present invention seeks to provide a mass-produced, tooth colored pre-fabricated crown, particularly useful in pediatric dentistry for treatment of primary teeth and permanent molars having extensive carious lesions.

There is thus provided in accordance with a preferred embodiment of the present invention an injection molded dental crown formed of an acetal homopolymer, which includes Polioxymethylene (POM) Thermoplastic Homopolymer.

In accordance with a preferred embodiment of the present invention, the injection molded dental crown is formed with depending side surfaces at least one of which defines an undercut.

Preferably, the depending side surfaces are flexible.

There is also provided in accordance with a preferred embodiment of the present invention a method for mass producing dental crowns comprising: providing a multi-element mold, employing the multi-element mold to injection mold the crown including depending side surfaces, at least one of which defines an undercut.

In accordance with a preferred embodiment of the present invention, the multi-element mode includes an ejector which is operative to eject the molded crown following opening of the multi-element mold.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
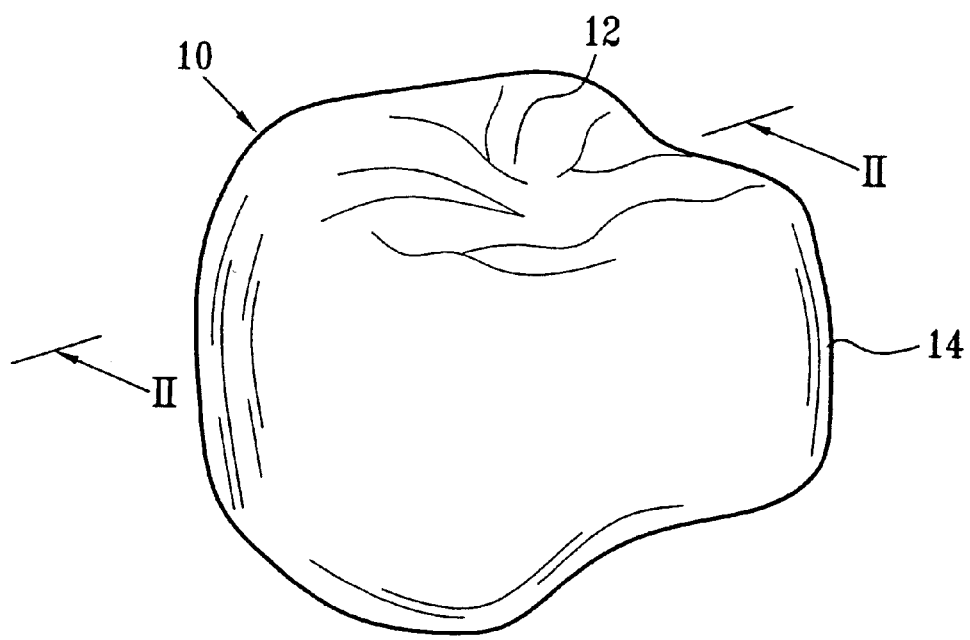
FIG. 1 is a simplified pictorial illustration of a dental crown formed of acetal homopolymer.
Figure 2:
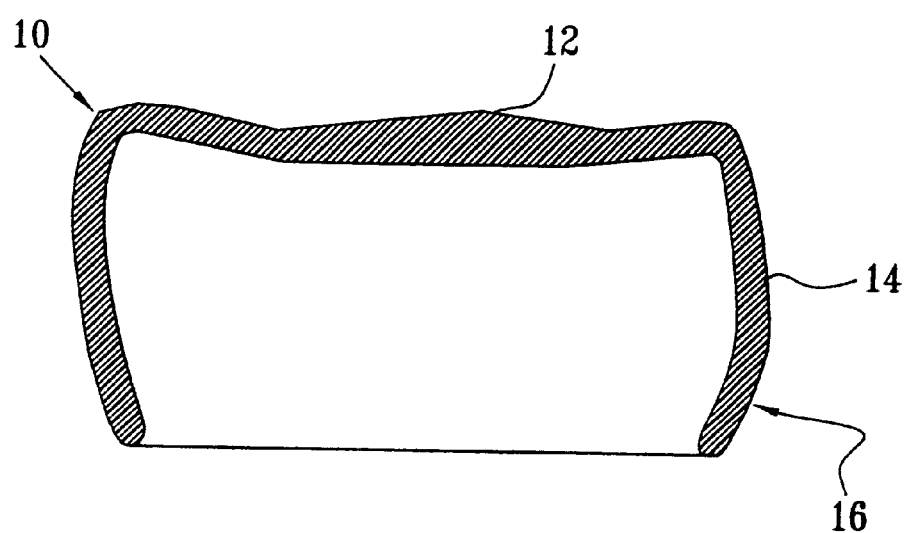
FIG. 2 is a sectional illustration of the dental crown of FIG. 1, taken along lines II—II in FIG. 1.

Reference is now made to FIG. 1, which is a simplified pictorial illustration of a dental crown formed of acetal homopolymer resin and to FIG. 2, which is a sectional illustration of the dental crown of FIG. 1, taken along lines II—II in FIG. 1.

As seen in FIGS. 1 and 2, there is provided in accordance with a preferred embodiment of the present invention an injection molded dental crown 10 formed of an acetal homopolymer resin. A preferred material for the crown is acetal homopolymer resin (DELRIN®) which is commercially available from DuPont.

As can be readily seen in FIGS. 1 and 2, the dental crown 10 is formed with a generally conventionally tooth shaped top surface 12 and depending side surfaces 14 at least one of which includes an undercut, which defines an inwardly directed bottom portion 16. Preferably, the depending side surfaces 14 are flexible. Crown 10 may readily be mounted, by conventional methods, such as through the use of dental cement in the mouth of a patient, typically a child, as part off treatment of primary teeth and permanent molars having extensive carious lesions It is a particular feature of the invention that crown 10 is of a color which generally matches of the patient's teeth.

The crown of the present invention is characterized by high tensile strength, high impact resistance and stiffness, excellent fatigue endurance and resistance to moisture, excellent dimensional stability and sufficient resilience and resistance to creep. It has the natural appearance of a vital tooth Reference is now made to FIGS. 3A, 3B and 3C, which are each simplified pictorial illustrations of apparatus for manufacturing a dental crown from acetal homopolymer resin in accordance with a preferred embodiment of the present invention in three operative orientations.

Figure 3A:
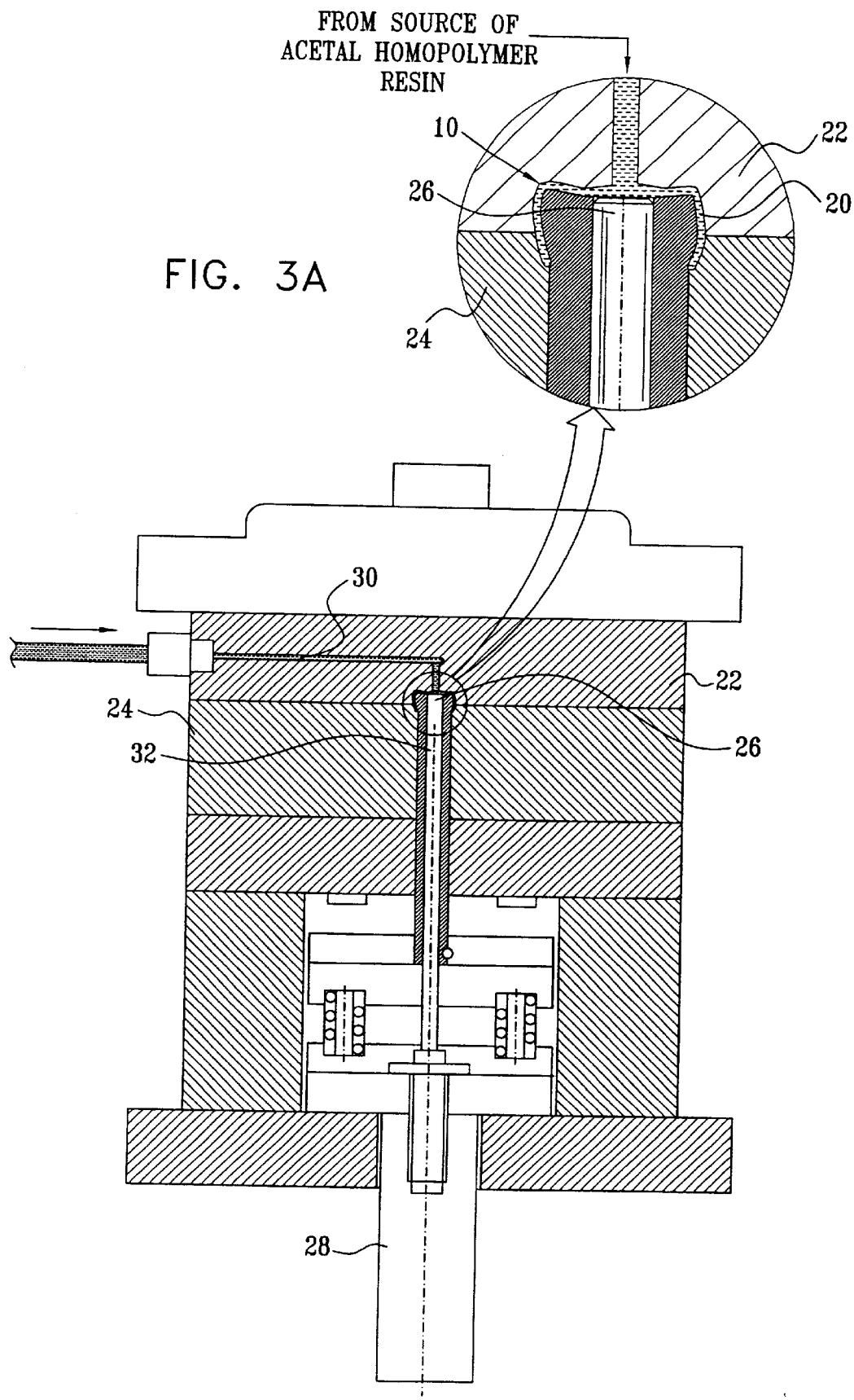
FIGS. 3A, 3B and 3C are each simplified pictorial illustrations of apparatus for manufacturing a dental crown from acetal homopolymer resin in accordance with a preferred embodiment of the present invention in three operative orientations.
Figure 3B:
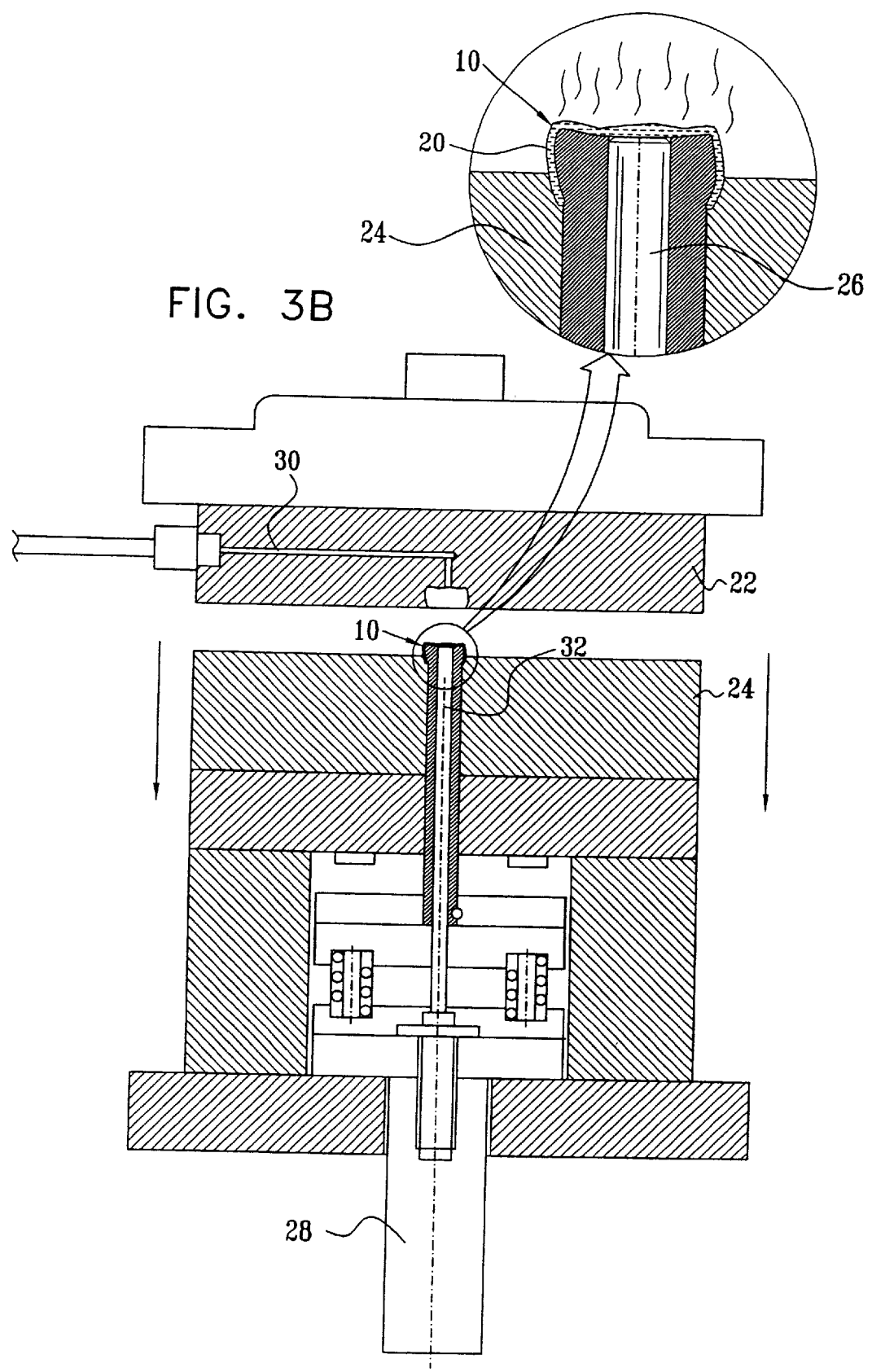
Figure 3C:
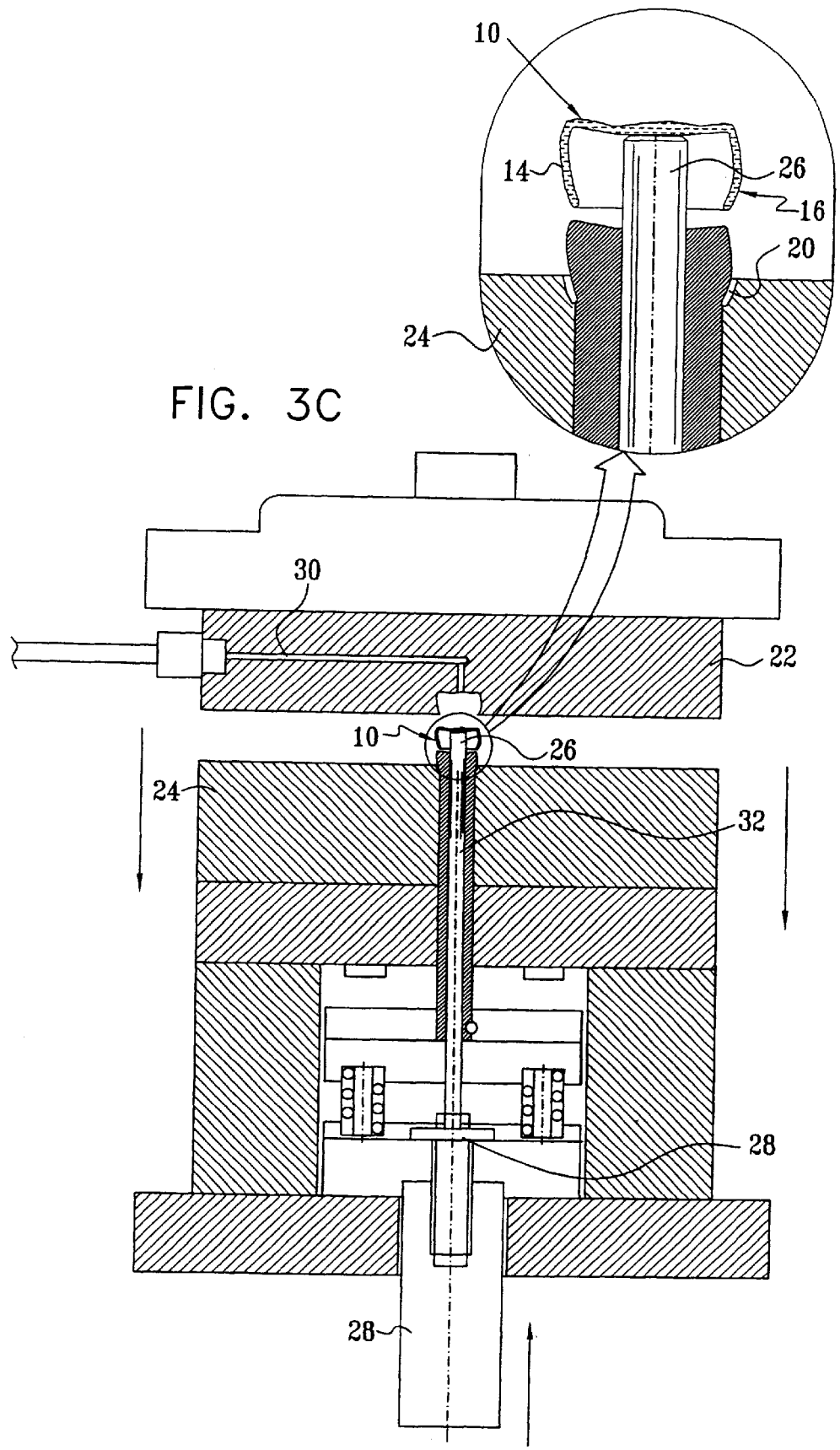

As seen in FIGS. 3A, 3B and 3C, the crown 10 is molded in a mold cavity 20 which is defined by a top mold element 22, a bottom mold element 24 and an ejector 26. The ejector 26 forms part of an internal mold element 32.

FIG. 3A shows the stage of molding when the top mold element 22 lies in tight engagement with the bottom mold element 24 and the ejector 26. The dental crown 10, which is fabricated on the ejector 26, is formed by the injection of acetal homopolymer resin material from a source of acetal homopolymer resin (not shown) into the mold cavity 20, via a channel 30 cut in the top mold element 22.

FIG. 3B shows an initial release stage wherein the bottom mold element 24 is separated from the top mold element 22, thus permitting removal of the molded crown 10 from cavity 20.

FIG. 3C shows an ejection stage wherein ejector 26, driven by a piston 28 moves upwardly relative to bottom mold element 24 and pushes crown 10 out of cavity 20. Due to the resilience of the depending side surfaces 14, the action of the ejector 26 is able to disengage the internal mold element 32 from the crown 10 notwithstanding the presence of inwardly directed bottom portion 16.

It will be appreciated by persons skilled in the art that the present invention is not limited by what has been particularly shown and described hereinabove. Rather the scope of the present invention includes both combinations and sub-combinations of the various features described hereinabove as well as variations and modifications which would occur to persons skilled in the art upon reading the specification and which are not in the prior art.

What is claimed is:

1. A dental crown formed of an acetal homopolymer resin comprising:

a tooth shaped top surface; and depending side surfaces, at least one of which includes an inwardly directed bottom portion, wherein said crown is formed by injection molding.

2. A dental crown according to claim 1 and wherein said depending side surfaces are flexible.

3. A dental crown formed of an acetal homopolymer resin, comprising depending side surfaces, wherein said side surfaces are flexible, and wherein said crown is formed by injection molding.

* * * * *

UNITED STATES PATENT AND TRADEMARK OFFICE
CERTIFICATE OF CORRECTION

PATENT NO.     : 6,592,373 B2
DATED          : July 15, 2003
INVENTOR(S)    : Uri L. Zilberman It is certified that error appears in the above-identified patent and that said Letters Patent is hereby corrected as shown below:

Column 2,
Line 8, "off" should read -- of --.

Signed and Sealed this

Sixteenth Day of November, 2004

JON W. DUDAS
*Director of the United States Patent and Trademark Office*